United States Patent [19]

Duffett

[11] Patent Number: Plant 5,986

[45] Date of Patent: May 12, 1987

[54] CHRYSANTHEMUM PLANT NAMED ENVY

[75] Inventor: William E. Duffett, Salinas, Calif.

[73] Assignee: Yoder Brothers, Inc., Barberton, Ohio

[21] Appl. No.: 765,515

[22] Filed: Aug. 14, 1985

[51] Int. Cl.[4] ..... A01H 5/00

[52] U.S. Cl. ..... Plt./77

[58] Field of Search ..... Plt./77

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Envy having flat capitulum form; decorative capitulum type; ivory and white ray floret colors; diameter across face of disbudded capitulum ranging from 10 to 12 cm. at maturity; uniform eight week photoperiodic flowering response to short days; short plant height when grown as a pinched disbudded pot mum; spreading branching pattern; tolerance of high summer 23° C. to 38° C. temperatures for bud initiation and flower development; and immature ray florets which are suffused with ivory.

3 Drawing Figures

1

The present invention comprises a new and distinct cultivar of *Chrysanthemum morifolium,* Ramat., named Envy.

Envy is a product of a planned breeding program which had the objective of creating new Chrysanthemum cultivars for pinched disbudded pot mum programs having decorative capitulum type, white floret color, eight week flowering response, and the ability to produce commercially acceptable quality in year round programs. Such traits in combination were not present or required improvements in previously available commercial cultivars.

Envy, identified as 82#64007, was originated from a cross made by William E. Duffett in a controlled breeding program in Salinas, Calif. in 1981. The female parent was Paragon, disclosed in U.S. Plant Pat. No. 3,368 and originated by the present inventor. The male parent of Envy, identified as 77280F01, was an induced mutation derived from Surf, disclosed in U.S. Plant Pat. No. 4,585.

Envy was discovered and selected as one flowering plant within the progeny of the stated cross by William E. Duffett in May 1982 in a controlled environment in Salinas, Calif.

The first act of asexual reproduction of Envy was accomplished when vegetative cuttings were taken from the initial selection in August 1982 in a controlled environment in Salinas, Calif. by a technician working under formulations established and supervised by William E. Duffett. Horticultural examination of selected units initiated June 1983 has demonstrated that the combination of characteristics as herein disclosed for Envy are firmly fixed and are retained through successive generations of asexual reproduction.

Envy has not been observed under all possible environmental conditions. The phenotype may vary significantly with variations in environment such as temperature, light intensity and day length. The observations, measurements and comparisons describe plants grown in Salinas, Calif. and Leamington, Ontario, Canada under greenhouse conditions which approximate those generally used in commercial practice.

The following traits have been repeatedly observed and are determined to be basic characteristics of Envy which in combination distinguish this chrysanthemum as a new and distinct cultivar:

2

(1) Flat capitulum form.

(2) Decorative capitulum type.

(3) Ivory and white ray floret colors.

(4) Diameter across face of capitulum ranging from 10 to 12 cm. at maturity.

(5) Uniform eight week photoperiodic flowering response to short days.

(6) Short plant height, requiring 2 long day weeks prior to pinch followed by 3 to 7 long days prior to short days, and 0 to 1 application of 2500 ppm B-9 SP in 7 to 14 days after the beginning of short days to attain a flowered plant height of 25 to 35 cm. in 6″ pots.

(7) Spreading branching pattern.

(8) Tolerance of high summer 23° C. to 38° C. temperatures.

(9) Immature ray florets suffused with ivory.

The accompanying photographic drawings depict typical leaf and inflorescence characteristics of Envy.

Sheet 1 is a color photograph of a plant of Envy grown as a pinched disbudded pot mum, with colors being as accurate as possible with renditions of this type.

Sheet 2 is a black and white photograph of three views of the inflorescence of Envy.

Sheet 3 shows the leaves of Envy in three stages of growth (mature, intermediate and immature).

Of the many commercial cultivars known to the present inventor the most similar in comparison to Envy is the female parent Paragon. Reference is made to attached Chart A which compares certain characteristics of Envy to those same characteristics of Paragon. Similar traits are type, form, color and branching pattern. Envy has a faster response, a shorter plant habit, smaller capitulum diameter, and its tolerance of high summer temperatures results in faster and more uniform response under high temperature.

In the following description, color references are made to The Royal Horticultural Society Colour Chart. The color values were determined between 11:30 and 11:45 a.m. on Nov. 28, 1984 under 380 foot-candle light intensity at Salinas, Calif.

Classification:

*Botanical.*—*Chrysanthemum morifolium,* Ramat., cv Envy.

*Commercial.*—Decorative disbud pot mum.

I. INFLORESCENCE

A. Capitulum:

*Form.*—Flat.

*Type.*—Decorative.

*Diameter across face.*—10 to 12 cm.

B. Corolla of ray florets:

*Color (general tonality from a distance of three meters).*—White.

*Color (upper surface).*—155D mature; 2C and 2D immature.

*Color (under surface).*—155D mature; 2C and 2D immature.

*Shape.*—Ranges from tubular, through all spoon shapes to fully flat form.

C. Corolla of disc florets:

*Color (mature).*—2B.

*Color (immature).*—154A.

D. Reproductive organs:

*Androecium.*—Present disc florets only; scant pollen.

*Gynoecium.*—Present both ray and disc florets.

II. PLANT

A. General appearance:

*Height.*—Short.

*Branching pattern.*—Spreading.

B. Foliage:

*Color (upper surface).*—147A.

*Color (under surface).*—147B.

*Shape.*—Shallow lobed. Slight to moderate serration.

CHART A

COMPARISON OF ENVY AND PARAGON

| CULTIVAR | RAY FLORET COLOR | CAPITULUM FORM AND TYPE | BRANCHING PATTERN |
|---|---|---|---|
| ENVY | IVORY IMMATURE WHITE MATURE | FLAT DECORATIVE | SPREADING |
| PARAGON | WHITE | FLAT DECORATIVE | SPREADING |

| CULTIVAR | DIAMETER ACROSS FACE OF CAPITULUM | PLANT HEIGHT | FLOWERING RESPONSE PERIOD | TEMPERATURE TOLERANCE |
|---|---|---|---|---|
| ENVY | 10 to 12 cm. | SHORT | EIGHT WEEKS | HIGH: 23° C. to 38° C. |
| PARAGON | 11 to 14 cm. | MEDIUM | NINE WEEKS | REQUIRES 15° C. MINIMUM |

COMPARISONS MADE OF PLANTS GROWN AS PINCHED DISBUDDED POT MUMS IN SALINAS, CALIFORNIA AND LEAMINGTON, ONTARIO, CANADA

I claim:

1. A new and distinct cultivar of *Chrysanthemum morifolium,* Ramat., plant named Envy, as described and illustrated, and particularly characterized as to uniqueness by the combined characteristics of flat capitulum form; decorative capitulum type; ivory and white ray floret colors; diameter across face of capitulum ranging from 10 to 12 cm. at maturity; uniform eight week flowering response; short plant height; spreading branching pattern; tolerance of high summer 23° C. to 38° C. temperatures for bud initiation and flower development; and by its immature ray florets which are suffused with ivory.

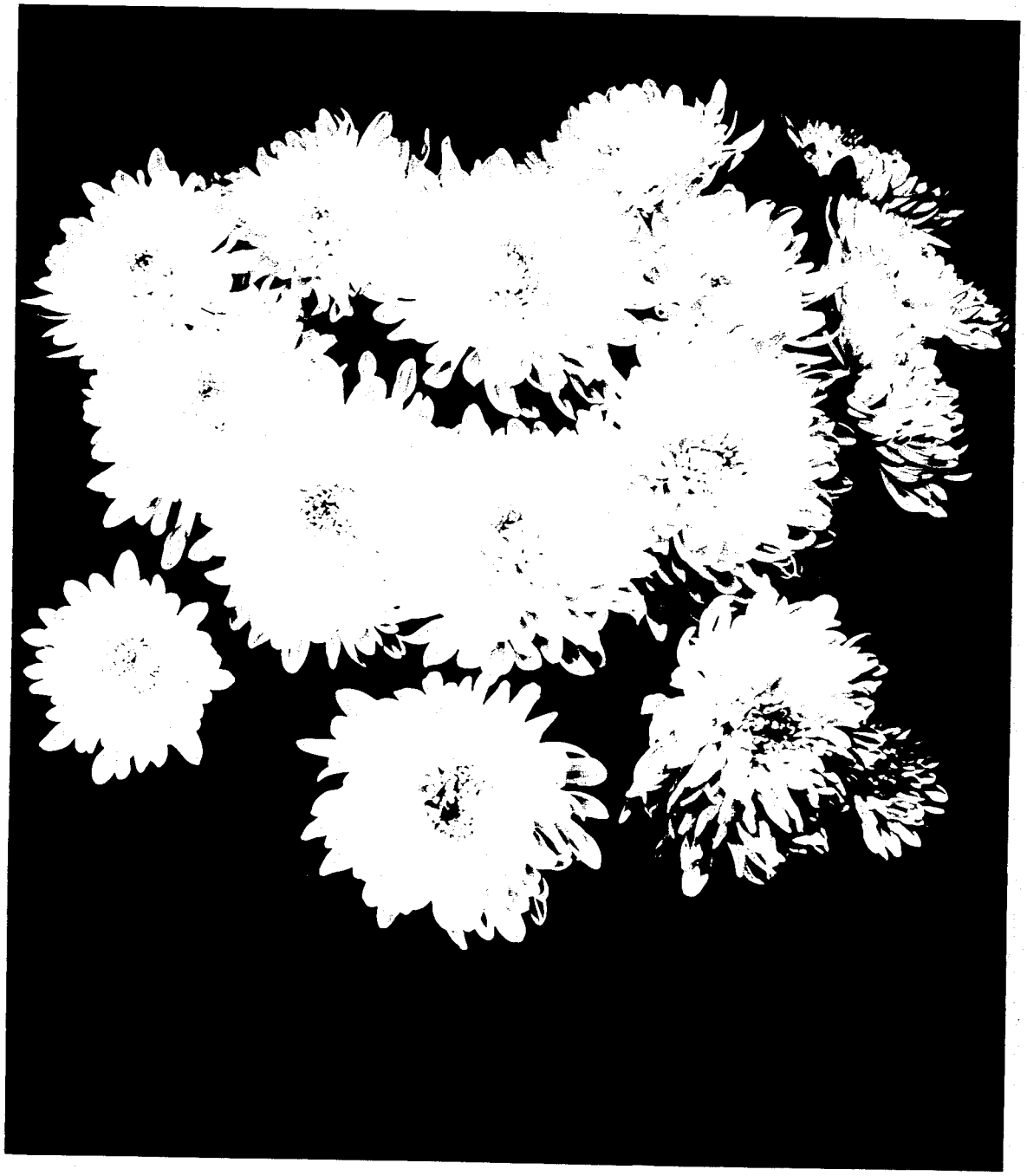

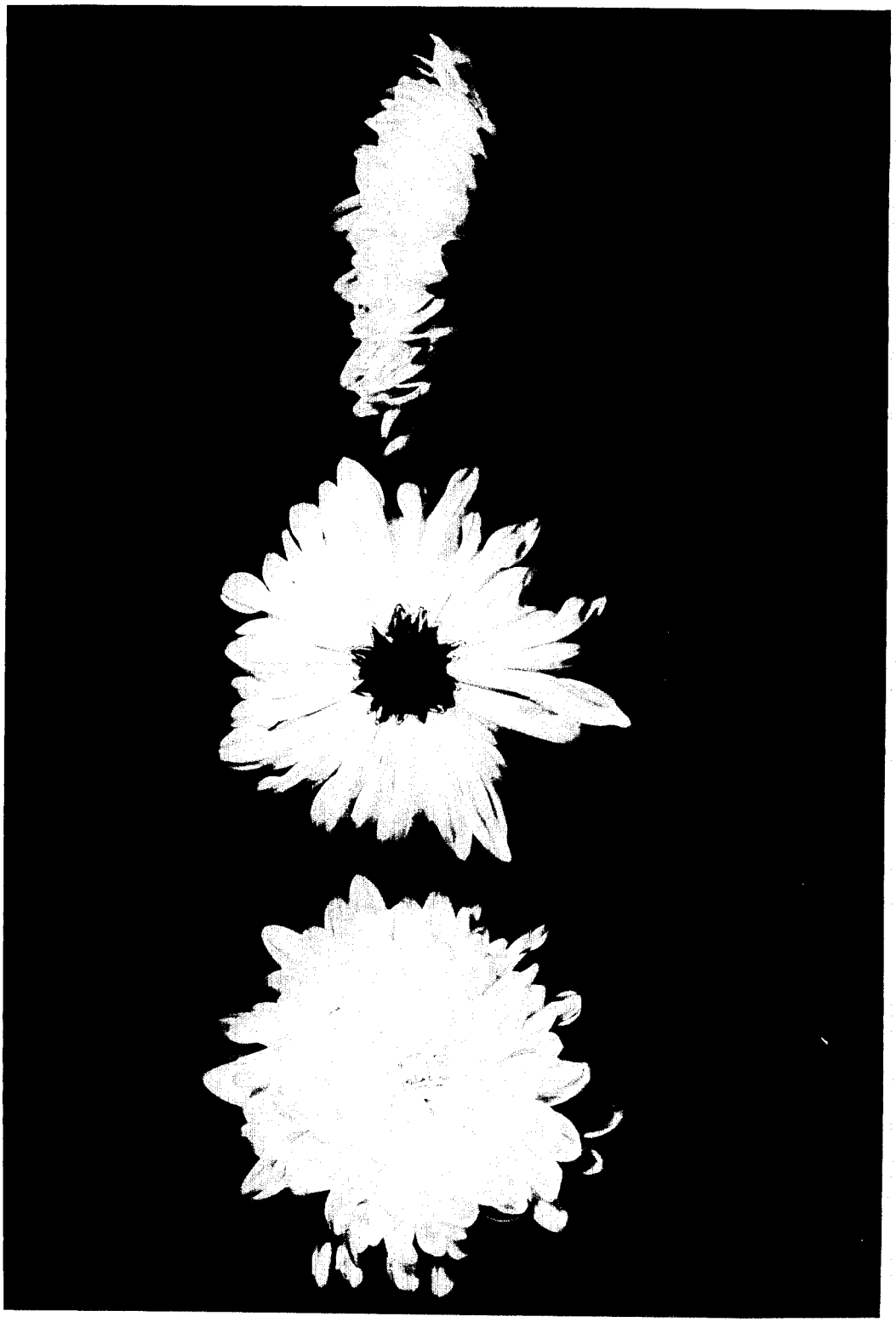

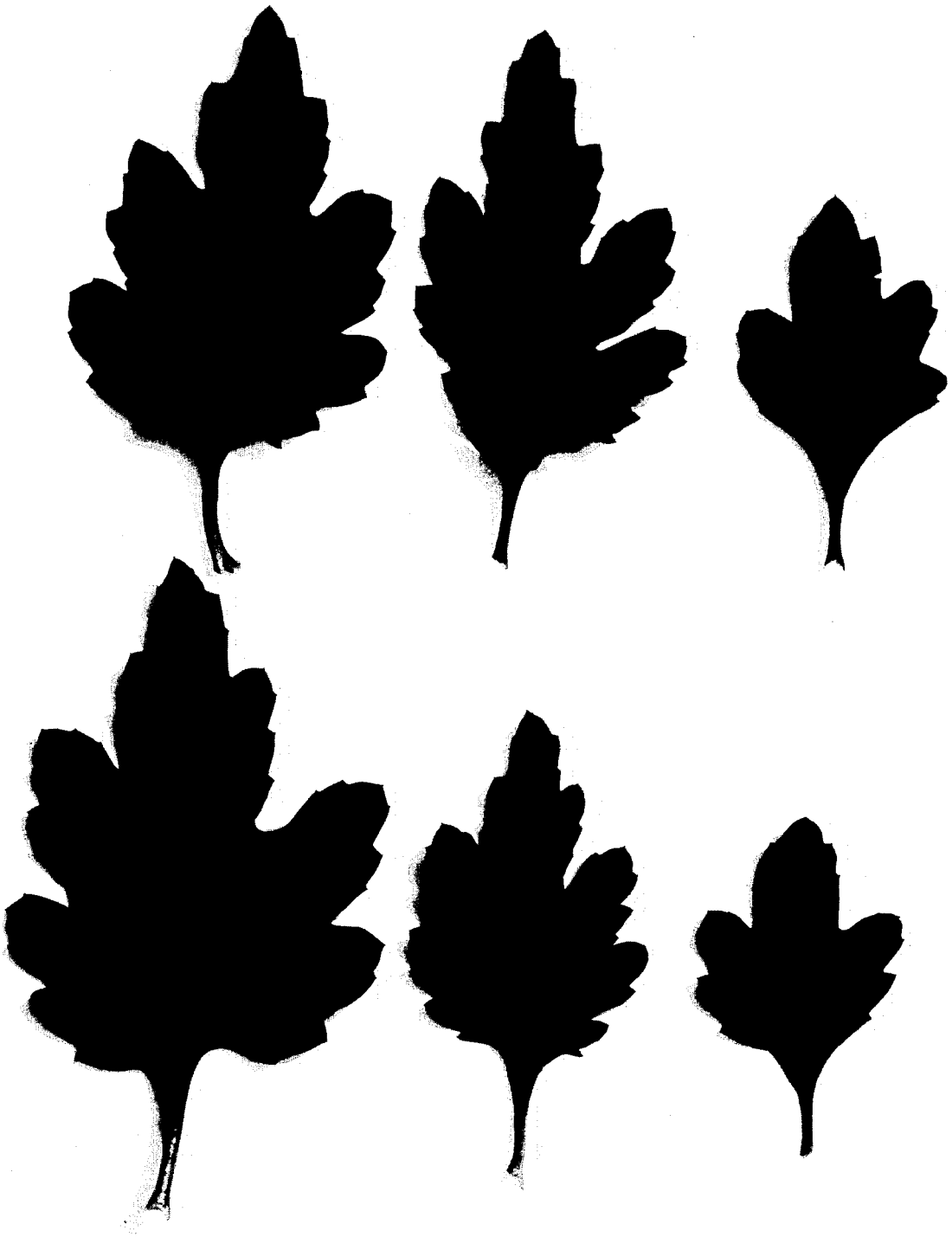

* * * * *